United States Patent [19]
Advani

[11] 4,119,412
[45] Oct. 10, 1978

[54] AMMONIA ABSORPTION PROCESS

[75] Inventor: Prem S. Advani, Conroe, Tex.

[73] Assignee: Texaco Development Corporation, New York, N.Y.

[21] Appl. No.: 843,400

[22] Filed: Oct. 19, 1977

Related U.S. Application Data

[62] Division of Ser. No. 644,696, Dec. 29, 1975, Pat. No. 4,091,218.

[51] Int. Cl.² .............................................. B01D 19/00
[52] U.S. Cl. ....................................................... 55/70
[58] Field of Search ...................................... 55/70, 68

[56] References Cited
U.S. PATENT DOCUMENTS

| | | | |
|---|---|---|---|
| 3,344,585 | 10/1967 | Hollowell | 55/70 |
| 4,013,431 | 3/1977 | Berkel et al. | 55/70 |

*Primary Examiner*—Bernard Nozick
*Attorney, Agent, or Firm*—Carl G. Ries; Thomas H. Whaley; James L. Bailey

[57] ABSTRACT

A process is disclosed whereby a gas stream from the process for the manufacture of a morpholine compound by the catalytic reaction of a dialkylene glycol with ammonia to form a morpholine compound in the presence of hydrogen is disclosed. The ammonia is scrubbed from the gas stream by using the dialkylene glycol feedstock as the scrubbing fluid. Thus dry hydrogen can be repressurized and used in the process as can the ammonia in the feedstock stream.

1 Claim, 1 Drawing Figure

U.S. Patent
Oct. 10, 1978
4,119,412
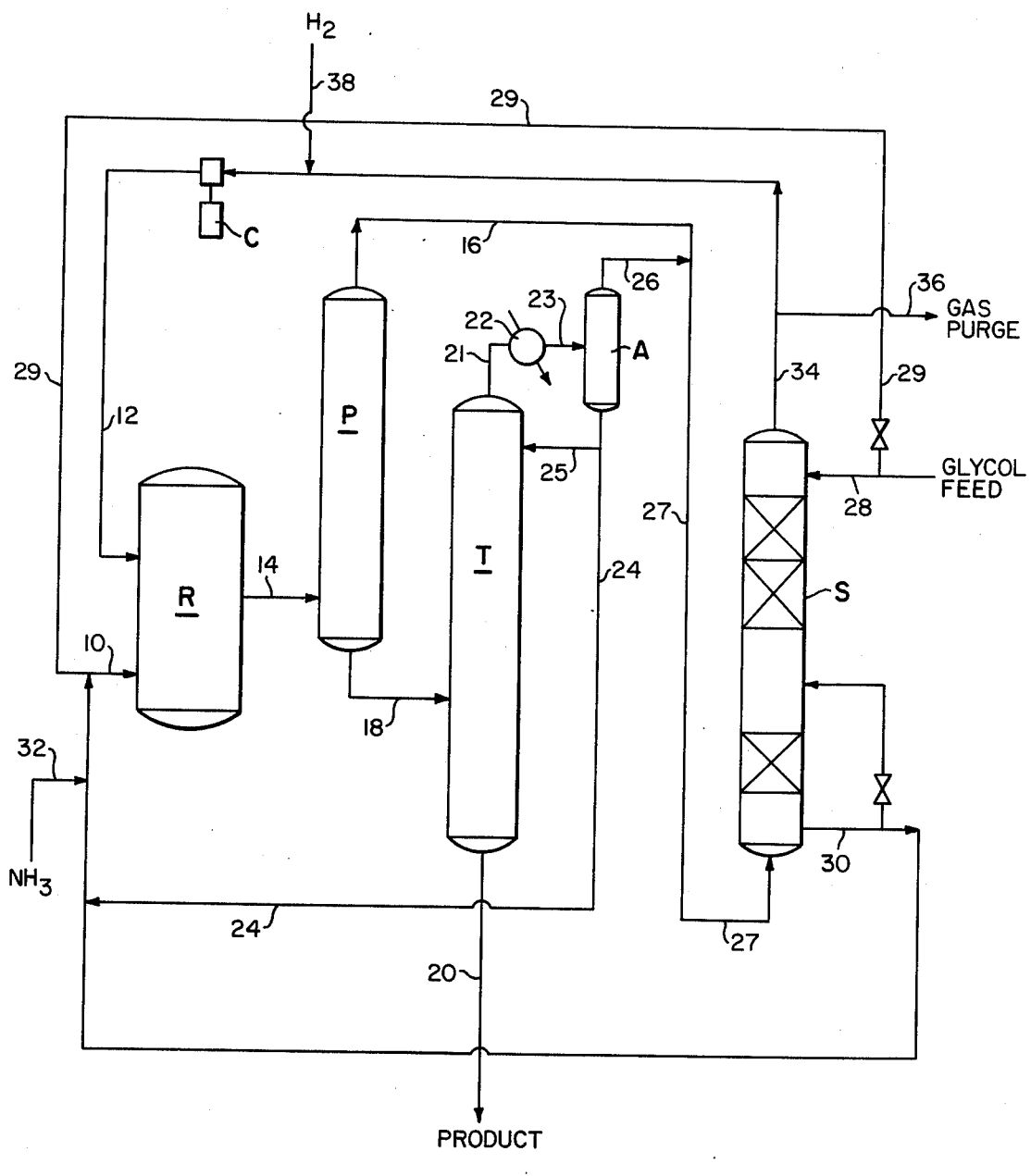
PRODUCT

AMMONIA ABSORPTION PROCESS

This is a division, of application Ser. No. 644,696, filed Dec. 29, 1975 now U.S. Pat. No. 4,091,218.

BACKGROUND OF THE INVENTION

This invention relates to an improvement in the process for the manufacture of a morpholine compound from the reaction of a dialkylene glycol with ammonia in the presence of hydrogen and a hydrogenation catalyst whereby hydrogen and unreacted ammonia are recovered and reused in the process. The process for the manufacture of morpholines to which this invention is most particularly adaptable is described in U.S. Pat. No. 3,151,112 and is applicable to the broadest description thereof.

In such a process a dialkylene glycol described by the formula:

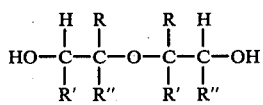

wherein R, R' and R" are hydrogen, alkyl or aryl, is reacted with ammonia in the presence of hydrogen and a hydrogenation catalyst to produce a morpholine compound. Suitable dialkylene glycols include diethylene glycol, dipropylene glycol, di-1, 2-butylene glycol, di-2, 3-butylene glycol, and the like, and the term morpholine compound is used in the generic sense and is meant to include the compounds from which the name is derived and the carbon substituted alkyl and aryl derivatives thereof. For example, this term includes morpholine and its mono, di, tri, and tetra alkyl or aryl substituted derivatives.

The process for the manufacture of morpholine as described in the above-identified patent involves a reaction at elevated temperatures and pressures. The reaction broadly taught occurs at between about 150° C. to about 400° C. and in a pressure range from about 30 to about 400 atmospheres though this invention is just as applicable to similar processes operating at other conditions. The reaction of the dialkylene glycol with ammonia occurs in the presence of hydrogen which must be present at least in substantial amounts for the efficient conduct of the morpholine process. As stated in the patent, hydrogen should contribute from about 10 to about 200 atmospheres of the reaction pressure.

The practice of the process is carried out in the presence of a suitable catalyst, generally classified as hydrogenation catalysts, or in another sense hydrogenation-dehydrogenation catalysts, many of which are disclosed in said U.S. Pat. No. 3,151,112. However, it will be understood that the practice of the invention described and claimed herein is adaptable to any process for the manufacture of morpholine by reacting a dialkylene glycol with ammonia in the presence of a catalyst and a hydrogen since, under such conditions, it is necessary for the efficient and economic manufacture of the product to recover hydrogen and ammonia for recycle to the process. Ammonia is introduced into the reaction in a large excess and hydrogen is consumed only slightly if at all. Thus, recovery and recycle is necessary.

Previously this recovery has been accomplished by scrubbing the gas stream, comprised generally of hydrogen, methane and ammonia, with water to separate the ammonia from the hydrogen so that hydrogen could be returned to the reactor through a compressor which would restore the pressure of the hydrogen to the level at which the reaction is conducted. After scrubbing, the hydrogen, including the methane stream, is saturated with water. The presence of water in such a hydrogen stream complicates matters since water creates a corrosion problem and condenses when the hydrogen is compressed.

Further, when water scrubbing is used to remove the ammonia it is necessary to attempt to separate the ammonia from water scrubbing material prior to the recycling of the ammonia to the reactor. Thus, some ammonia is lost during the stripping of ammonia from water making it necessary to dispose of ammonia-contaminated water in a manner to protect the environment, often to the extent of incinerating the waste stream. This contributes to a loss in efficiency of the plant by requiring considerable additional energy and capital investment to accomplish an ecologically safe disposal of the waste material.

Accordingly, it is an object of this invention to provide a process whereby efficient use can be made of gases from the process of the manufacture of morpholine compounds from the catalytic reaction of a dialkylene glycol with ammonia in the presence of hydrogen. It is a further object of this invention to effect substantially quantitative recovery of ammonia from the process for recycling to the reactor.

It is still further objective of this invention to provide for the recovery of hydrogen in a substantially anhydrous condition for recycle to the reactor. It is yet another object of this invention to recover ammonia from the off gases of the morpholine process thereby avoiding the release of such material upon the environment.

SUMMARY OF THE INVENTION

In its broadest aspects this invention relates to a process for recovering ammonia from a gas stream containing ammonia and hydrogen, particularly from processes for the manufacture of a morpholine compound by the reaction of a dialkylene glycol with ammonia in the presence of hydrogen and similar processes such as ammonolysis reaction carried out in the presence of hydrogen or the hydrogentation of acrylonitriles, i.e., the ammonolysis of alcohols and the manufacture of piperazines. Such recovery is effected by contacting the gas stream containing hydrogen, ammonia, and usually methane with a dialkylene glycol, preferably the dialkylene glycol feedstock for the morpholine process whereby the ammonia is absorbed from the gas stream leaving substantially anhydrous hydrogen and methane, with a small amount of ammonia, to be recycled through a process compressor to the reactor in the morpholine process.

In the process for the manufacture of a morpholine compound or a piperazine compound, there are gas streams released from the process equipment as described more completely hereinafter containing hydrogen, ammonia and methane. These streams are collected and passed through a scrubbing tower, generally in counter-current flow, where they are contacted with a dialkylene glycol feedstock for the morpholine reaction. This dialkylene glycol exits the scrubbing tower rich in ammonia removed from the gas stream and the rest of the gas stream, principally hydrogen and methane, leaves the scrubbing tower substantially free of water for return to the compressor for the process whereby they are brought up to the pressure of the reaction vessel. The dialkylene glycol stream, rich in ammonia, is used as the reaction feed for the reactor with the relative concentrations of the components being adjusted to the proper proportions by addition of fresh ammonia.

DESCRIPTION OF THE DRAWING

The attached drawing is a schematic diagram of the process and apparatus of this invention with the obvious valves, fittings, and gauges omitted therefrom.

DETAILED DESCRIPTION OF THE INVENTION

This invention is an improvement in the process for the manufacture of a morpholine compound through the catalytic reaction of a dialkylene glycol with ammonia. The reaction is carried out at superatmospheric pressures, usually between about 30 and about 400 atomspheres and elevated temperatures ranging between 150° C. and about 400° C. This reaction is conducted under a partial pressure of hydrogen and to fully realize the efficiencies of the catalytic process, hydrogen and unreacted feed materials are recovered and recycled through the process.

In general, once the reaction is completed the reaction products together with hydrogen and other by-products of the reaction are separated to remove the gaseous materials from the liquid reaction products and then recovery of the materials to be recycled is accomplished. The liquid products are separated from the ammonia and other gases, which gases are combined and removed in a recovery section of the process. Heretofore such recovery section of the process required the use of a plurality of scrubbing towers to separate ammonia from hydrogen in addition to a stripping tower to recover the ammonia from water used in the scrubbing operation. In the practice of this invention, the dialkylene glycol feed is used to accomplish the scrubbing of the ammonia from the hydrogen. This results in a number of advantages, including the prevention of the hydrogen from becoming saturated with water and also the substantially quantitative recovery of ammonia, thus eliminating the loss of ammonia previously experienced plus eliminating the expense of disposing of a water waste effluent which is contaminated with ammonia; often only disposable by incineration.

The improved process of this invention will be discussed hereinafter with particular reference to the drawing appended hereto and, for simplicity, the discussion will be limited to the preferred embodiment of this invention wherein morpholine is prepared by the reaction of diethylene glycol with ammonia in the presence of a suitable hydrogenation-dehydrogenation catalyst under an atmosphere having a partial pressure of hydrogen. The basic reaction and process is described in U.S. Pat. No. 3,151,112, for example, which is incorporated herein by reference, and the specific reaction parameters of the reaction discussed therein will not be repeated here. Particular attention will be given to the novel aspects of this invention with respect to the recovery of hydrogen and ammonia for reuse in the process.

The reaction of the process of this invention takes place in the reactor R. The reactants, diethylene glycol and ammonia enter, in proper proportions, as described in U.S. Pat. No. 3,151,112 through line 10 to contact a suitable catalyst in the presence of hydrogen. The pressure of the reactor R is maintained in part by the introduction of hydrogen through line 12 from the compressor C. The reaction of the diethylene glycol and ammonia occurs in the reactor R and the reaction products and by-products are removed from reactor R through line 14 and enter a high pressure separator P. The pressure is maintained in the high pressure separator P by a back pressure valve, not shown, in the gaseous effluent line 16. The high pressure separator P generally operates at a pressure between about 5 and about 200 atmospheres, preferably between about 1000 and 2500 lb. per sq. in. to separate the products from the reactor R entering through line 14 into a gaseous overhead stream which exits through line 16 and a liquid bottom stream containing the morpholine, other liquid reaction products, water and most of the ammonia exiting through line 18. The overhead gaseous stream 16 typically contains hydrogen, methane and some ammonia. The liquid stream, containing ammonia and other gases absorbed therein, moves through line 18 to an ammonia recovery tower T which is used to further strip the gaseous materials from the liquid reaction products of the reactor R. This recovery tower T is typically a simple distillation column but other well-known gas-liquid separation means are useful as the tower T. The pressure conditions of this tower are maintained through a back pressure control valve, not shown, on the gaseous effluent side of the tower as hereinafter described. The tower T is operated at a temperature and pressure such that the morpholine, excess diethylene glycol and other liquid products are recovered from the bottom of the tower through line 20 and separated in known process equipment in a manner known to those skilled in the art. The ammonia and other gaseous materials, such as hydrogen and methane, exit the tower T through line 21. The tower T is preferably operated at from about 120 to about 150 psig pressure and a temperature from about 280° F. to about 420° F. for efficient separation of gaseous materials from product. It is preferred that the gases in line 21 pass through condenser 22 where most of the ammonia is condensed to a liquid which is carried through line 23 to an accumulator A where the condensed ammonia is separated from the gas stream. The condensed ammonia exits the accumulator and is recycled to the reactor R through line 24. A portion of the liquid ammonia is fed to tower T through line 25 as a reflux. Of course, the liquid ammonia can be recycled to the reactor and fed back to the tower directly from the condenser 22 but the presence of the accumulator A in the system is preferred. The gases, principally hydrogen and methane, with some ammonia, exit the accumulator A in line 26 through a back pressure regulator, not shown, which holds the tower system at sufficiently high pressure to condense the ammonia. This pressure condition is important to the recovery of ammonia regardless of whether the scrubbing system of this invention or a prior art water scrubber is used.

The gaseous effluent from the high pressure separator P and the ammonia recovery tower T exiting through lines 16 and 26, respectively, are collected in conduit 27 and then conducted to the scrubbing process of this invention to separate ammonia from the hydrogen for recycle.

This separation occurs in the practice of this invention as hereinafter described. The gaseous stream which contains essentially hydrogen, ammonia and methane enters a suitable scrubbing tower S through line 27. The stream entering through line 27 generally contains from about 20 to about 55 mol percent, usually from about 40 to about 50 mol percent, of ammonia, from about 30 to about 60 mol percent hydrogen with from about 8 to about 20 mol percent methane.

The scrubbing tower S can be of any appropriate design and is preferably packed with materials such as rings, saddles or other well-known suitable packing materials. However, the scrubbing tower S could suitably be a multiple plate scrubbing tower which provides for upward flow of the gas entering through line 27 and downward flow of the scrubbing fluid.

Depending upon design considerations, of course, the scrubber S will preferably have a plurality of theoretical stages which are easily calculated by the skilled engineer from solubility data with respect to the ammonia and dialkylene glycol, in this case diethylene glycol used as the feed for the morpholine process. While the gases enter the bottom of the scrubber S through line 27, the diethylene glycol is fed to the scrubber S through line 28 at the top of the tower so that it percolates downwardly through the scrubbing tower S contacting, in countercurrent flow, the gases rising through the tower. The glycol, which can also be recovered feedstock being recycled to the reactor R containing some intermediate reaction products recovered from the product stream 20, is fed to the scrubbing tower S in the rate at which it is to be fed to the reactor R since, unless the by-pass line 29 for the glycol is used, it is a preferred embodiment of this invention that the entire amount of diethylene glycol to be fed to the reactor passes through the scrubber S to ensure substantially complete removal of ammonia from the gas stream, thus minimizing the amount of liquefiable material to pass through the compressor C. This also has the advantage of providing an excess of diethylene glycol necessary to remove the ammonia in order to compensate for any possible gas surges from the reaction section of the process. While lesser amounts of the glycol can be calculated to provide an amount to provide substantially complete recovery of the ammonia, it is preferred to operate in the above manner. Even less glycol can be used, but this would result in increased loading in the hydrogen stream.

The glycol flowing downwardly through the scrubbing tower S absorbs the ammonia from the gas stream moving upwardly. The diethylene glycol, rich in ammonia, exits the tower through line 30 and can be directly transmitted through line 30 to empty into line 10 and then to the reactor R to provide the feedstock for such reaction. Should it be necessary to increase the proportion of ammonia in the feed stream to the reactor over that available from lines 30 and 24, such fresh ammonia can be added preferably into line 30 through line 32. It will be understood, however, by those of ordinary skill in the art that such ammonia could be added directly to the reactor R or directly to line 10 through an appropriate manifold.

The gas stream, now lean in ammonia, exits the scrubbing tower S through line 34 and will typically contain hydrogen, methane and only small amounts of ammonia. Since methane is formed in the reactor R and moves through the balance of the system as a substantially inert ingredient it will build up over a period of cycles in the hydrogen stream and then should be purged from the system. In the operation of the process most efficiently it is preferred that the methane level remain below about 30 mol percent of the gaseous stream in line 34. The hydrogen content of such gaseous stream, lean in ammonia, should be maintained at a level of at least about 70 mol percent and, preferably, about 80 mol percent for most efficient operation of the process. Thus, the hydrogen stream in line 34 must be purged through line 36. Since the purge stream is comprised almost entirely of combustible materials, it can be economically utilized for fuel to incinerate other wastes or burned for fuel to generate plant steam. Thus, the purged stream provides an economic advantage with respect to recovery of heating values.

Should additional hydrogen be necessary in order to maintain the desired partial pressure of hydrogen in the reactor R, fresh hydrogen can be added to line 34 through line 38 prior to the entry of the gases in line 34 to the compressor C. The hydrogen is compressed in compressor C and exits through line 12 and into the reactor as hereinbefore described. As an optional feature to improve the efficiency of the overall process, the liquid stream 30 exiting the scrubber S may appropriately have a recycle stream 40 which diverts a portion of the liquid stream in line 30 back into an intermediate point of the scrubbing tower S to improve the efficiency of removal of ammonia from the hydrogen. It is preferred that this recycle stream 40 be cooled prior to introduction into the tower in order to boost absorption efficiency since ammonia has a high heat of absorption.

Also, though not shown, it is advantageous to employ a surge tank in line 30 which would hold substantial amounts of diethylene glycol, rich in ammonia, such that, should it be necessary to shut down the scrubber from operation momentarily using a diethylene glycol feed, the reactor R would not necessarily have to be shut down since it could draw upon feed in such a surge tank. Further, the same is true of the hydrogen return line 34 which can appropriately have a pressure vessel which would store hydrogen before returning it to the compressor.

The upper limit of the pressure at which the scrubber S is operated is determined by the pressure of the tower T unless some means is inserted in line 24 to boost the pressure of the gases. Preferably, the gas enters the scrubber S at its line pressure out of the accumulator A which, of course, is less than that of the tower T, and most preferably, the scrubber S is operated at from about 30 to about 150 psig. While the scrubber S may be satisfactorily operated in a range of from about 30 to about 450 psig., little improvement in scrubbing efficiency is experienced and equipment cost is increased.

To further exemplify the operation of the above-described scrubbing process in a preferred embodiment of this invention wherein diethylene glycol is reacted with ammonia to produce morpholine the inlet gas enters the scrubber S through line 24 containing 46 mol percent hydrogen, 11 mol percent methane and 43 mol percent ammonia at a total mol flow rate of 72 mols per hour. Diethylene glycol is introduced into the top of the scrubber S at 18 gallons a minute at about 90° F. Since the heat of solution of ammonia in diethylene glycol is high, the liquid temperature of the diethylene glycol rich in ammonia exiting the scrubber is about 160° F. The outlet gas, exiting at a flow rate of 41.2 mols an hour, contains 80.1 mol percent hydrogen, 19.4 mol percent methane and 0.5 mol percent of ammonia. The liquid flow from the scrubbing step consists of 24.4 mol percent ammonia and 75.6 mol percent diethylene glycol. Thus, with 522 lb. of ammonia entering the scrubber system per hour, 518.5 lb. is removed from the hydrogen stream and recovered in the diethylene glycol stream. No ammonia is lost to the sewer and a dry hydrogen stream is returned to the condenser. In an actual operation of the tower with a diethylene glycol flow rate of 18 gallons per minute with the scrubber operation at 40 psig, 421 pounds per hour of ammonia was absorbed from a loading of 432 pounds per hour (49.5 mol percent ammonia). The scrubber bottoms temperature was about 140° F. and the outlet gas stream contained 2.6 mol percent ammonia.

Thus, it can be seen from the foregoing that the ammonia recovery is substantially complete and the practice in the process of this invention and that there is no necessity to dispose of any such material as waste. Also, the hydrogen recovered is in a stream substantially free of ammonia and water, thus avoiding the great corrosion problems heretofore prevalent. One of ordinary skill in the art may take many obvious modifications of the above-described invention as hereinafter claimed without departing from the scope and spirit thereof.

I claim:

1. The process for separating ammonia from hydrogen and methane in a gas stream produced in a catalytic ammonolysis reaction in the presence of hydrogen which comprises the steps of:
   a. contacting, in counter current flow, the gas stream with a dialkylene glycol in a packed tower operated at a pressure of from about 30 to about 150 psig;
   b. recovering a liquid bottoms stream of the glycol rich in ammonia;
   c. recovering a gaseous overhead stream consisting essentially of hydrogen and methane.

* * * * *